US008257578B2

(12) United States Patent
Teramoto et al.

(10) Patent No.: US 8,257,578 B2
(45) Date of Patent: Sep. 4, 2012

(54) ANOMALY DIAGNOSING APPARATUS AND ANOMALY DIAGNOSING METHOD FOR GAS SENSOR

(75) Inventors: Satoshi Teramoto, Aichi (JP); Shigeki Mori, Gifu (JP); Hiroki Inouchi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 418 days.

(21) Appl. No.: 12/571,928

(22) Filed: Oct. 1, 2009

(65) Prior Publication Data

US 2010/0084287 A1 Apr. 8, 2010

(30) Foreign Application Priority Data

Oct. 2, 2008 (JP) ................................ 2008-257446

(51) Int. Cl.
*G01N 27/41* (2006.01)
*G01N 27/26* (2006.01)

(52) U.S. Cl. ........ 205/785; 204/401; 204/424; 204/406; 73/23.31; 219/482

(58) Field of Classification Search .......... 204/421–429, 204/401; 219/482–506; 205/785; 73/23.31
See application file for complete search history.

(56) References Cited

U.S. PATENT DOCUMENTS

| 6,120,677 | A | 9/2000 | Yamada et al. | |
|---|---|---|---|---|
| 7,340,942 | B2 | 3/2008 | Matsuo et al. | |
| 2002/0179594 | A1* | 12/2002 | Hada et al. | 219/494 |
| 2005/0040040 | A1* | 2/2005 | Wahl et al. | 204/427 |
| 2006/0219553 | A1* | 10/2006 | Ieda et al. | 204/424 |
| 2006/0237315 | A1 | 10/2006 | Matsuo et al. | |

FOREIGN PATENT DOCUMENTS

| JP | 10048180 A | 2/1998 |
|---|---|---|
| JP | 2006300923 A | 11/2006 |
| JP | 2006308328 A | 11/2006 |
| JP | 2006343317 A | 12/2006 |

* cited by examiner

*Primary Examiner* — Jeffrey T Barton
*Assistant Examiner* — Jennifer Dieterle
(74) *Attorney, Agent, or Firm* — Sughrue Mion, PLLC

(57) ABSTRACT

An anomaly diagnosing apparatus and method for a gas sensor which includes a heater control section; a measurement section which outputs a detection signal for detecting an internal resistance of the gas sensor through a solid electrolyte via connection terminals and the electrodes within the gas sensor and which measures the internal resistance of the gas sensor based on a response signal input via the connection terminals in response to the output of the detection signal; and a diagnosing section which heats the solid electrolyte by use of the heater control section, obtains, after the start of heating, a first time required to reach a first resistance and a second time required to reach a second resistance different from the first resistance, and determines whether or not the gas sensor is anomalous by comparing a predetermined threshold value and a ratio of the first to second times.

6 Claims, 9 Drawing Sheets

ANOMALY DIAGNOSING APPARATUS AND ANOMALY DIAGNOSING METHOD FOR GAS SENSOR

BACKGROUND OF THE INVENTION

1. Field of the Invention

The present invention relates to an apparatus and method for diagnosing an anomaly of a gas sensor.

2. Description of the Related Art

Conventionally, in order to reduce the amount of CO, $NO_X$ and HC contained in exhaust gas of an internal combustion engine, a technique has been employed of detecting the concentration of a specific component (e.g., oxygen concentration) within the exhaust gas, and controlling the air-fuel ratio of a gas mixture supplied to the internal combustion engine in accordance with the detected concentration. For example, a lamda sensor in which a solid electrolyte is used as a sensor element and whose output assumes one of two values (representing rich and lean states, respectively) or a full range air-fuel ratio sensor is used as a gas sensor for detecting the concentration of the specific component within the exhaust gas.

In general, these gas sensors are configured as follows. A plate-shaped or bar-shaped sensor element is held within a cylindrical tubular metallic shell such that a gas detection section at the front end of the sensor element is exposed; and the exposed portion is covered with a protective cover. Electrodes for outputting a signal representing the concentration of a gas are provided on the surface of a rear end portion of the sensor element, and connection terminals of lead wires for leading the signal outside the gas sensor are in contact with the electrodes (refer to Patent Documents 1 and 2).

[Patent Document 1] Japanese Patent Application Laid-Open (kokai) No. 2006-300923
[Patent Document 2] Japanese Patent Application Laid-Open (kokai) No. 2006-308328
[Patent Document 3] Japanese Patent Application Laid-Open (kokai) No. 2006-343317
[Patent Document 4] Japanese Patent Application Laid-Open (kokai) No. H10-48180

As described above, the signal which represents the concentration of the gas is output outside the gas sensor via contact interfaces between the electrodes of the sensor element and the connection terminals of the lead wires. Therefore, if either of the contact interfaces has a contact resistance equal to or greater than a prescribed level, the contact resistance adversely affects the output of the gas sensor, whereby accuracy in measurement of the gas concentration is reduced.

SUMMARY OF THE INVENTION

The present invention has been made to address the above-described problems, and an object thereof is to diagnose an anomaly of a gas sensor which is caused by a high contact resistance between electrodes and connection terminals disposed within the gas sensor.

The above object of the present invention has been achieved by providing an anomaly diagnosing apparatus for diagnosing an anomaly of a gas sensor comprising a gas sensor element which includes a solid electrolyte and electrodes for outputting a signal representing an electrical characteristic of the solid electrolyte; connection terminals which contact the electrodes so as to lead the signal outside the gas sensor; and a heater which heats the solid electrolyte, the anomaly diagnosing apparatus comprising: a heater control section which controls the heater; a measurement section which outputs a detection signal for detecting an internal resistance of the gas sensor through the solid electrolyte and via the connection terminals and the electrodes and which measures the internal resistance of the gas sensor on the basis of a response signal which is input via the connection terminals in response to the output of the detection signal; and a diagnosing section which heats the solid electrolyte by use of the heater control section, obtains, after the start of heating, a first time required for the internal resistance, as measured by the measurement section, to reach a first resistance and a second time required for the internal resistance to reach a second resistance different from the first resistance, and determines whether or not the gas sensor is anomalous by comparing a predetermined threshold value with a ratio of the first to second times.

In the above-described mode, anomaly diagnosis is carried out by comparing a predetermined threshold value with a ratio of the times required for the internal resistance of the gas sensor to reach two different resistance values after the start of heating. Since the anomaly diagnosis is carried out based on the ratio of the time required for the internal resistance of the gas sensor to reach two different resistance values, an anomaly of the gas sensor caused by a high contact resistance can be diagnosed accurately and quickly. This is so even in the case of individual differences in gas sensors of the same model number (individual differences mainly due to manufacturing variations) resulting in variation of the first and second times.

In a preferred embodiment of the anomaly diagnosing apparatus for the gas sensor described above, the second resistance is $100\Omega$ or less, and the first resistance is greater than the second resistance by $250\Omega$ or more. When the difference between the first resistance and the second resistance is $250\Omega$ or greater, an anomaly of the gas sensor caused by a high contact resistance can be diagnosed more accurately.

In a preferred embodiment of the anomaly diagnosing apparatus for the gas sensor described above, the anomaly diagnosing apparatus further comprises a sensor temperature estimation section that estimates, before the heater control section begins control of the heater, whether the gas sensor is at a predetermined temperature or lower with reference to a sensor temperature parameter, and that allows the diagnosing section to execute the gas sensor diagnosis only when the sensor temperature estimation section determines that the gas sensor is at the predetermined temperature or lower.

In the present invention, since the anomaly diagnosis is carried out by comparing the ratio of the first to second times with the predetermined threshold value, the calculated ratio values can vary depending on the temperature of the gas sensor prior to the time that the heater control section begins control of the heater. As a result, the accuracy of the anomaly diagnosis may decline. Such a decrease in accuracy of the anomaly diagnosis can be restrained by providing the above-described sensor temperature estimation section and allowing the diagnosing section to execute the gas sensor diagnosis only when the sensor temperature estimation section determines that the gas sensor is at the predetermined temperature or lower. The "sensor temperature parameter" is information relating to the temperature state of the gas sensor temperature before control of the heater begins. For example, if the gas sensor is mounted in the exhaust pipe of an internal combustion engine of a vehicle or the like, any of the temperature of chilled water circulating in a water jacket for an internal combustion engine, the temperature of the exhaust pipe, or the elapsed time (a stopping time) from the end of a previous operation of the internal combustion engine, for example, may be used as the sensor temperature parameter.

Notably, the present invention can be practiced not only in the above-described mode (i.e., in the form of the above-described anomaly diagnosing apparatus), but also in other modes (e.g., in the form of an anomaly diagnosing method for a gas sensor or a computer program for diagnosing an anomaly of a gas sensor). The computer program may be stored on a computer-readable recording medium.

Further, in the present invention, the internal resistance of the gas sensor may be measured by supplying a transient current signal to the solid electrolyte and the electrodes, as a detection signal, and calculating the internal resistance based on a change in input signal voltage as a response signal. Alternatively, the internal resistance of the gas sensor may be measured by supplying a transient voltage signal to the solid electrolyte and the electrodes, as a detection signal, and calculating the internal resistance based on a change in input signal current as a response signal.

DESCRIPTION OF REFERENCE NUMERALS

Figure 1:
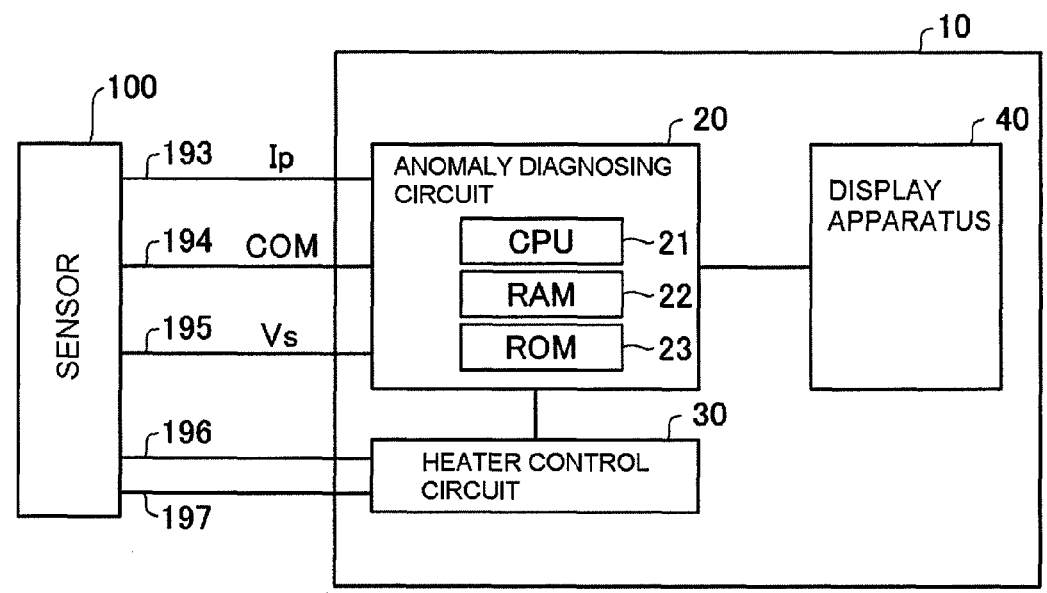
FIG. 1 is a block diagram schematically showing the configuration of an anomaly diagnosing apparatus 10.

Reference numerals used to identify structural features shown in the drawings include the following.

10 . . . anomaly diagnosing apparatus
20 . . . anomaly diagnosing circuit
30 . . . heater control circuit
40 . . . display apparatus
100 . . . gas sensor
110 . . . metallic shell
120 . . . gas sensor element
121 . . . gas detection section
123 . . . heater section
125 . . . sensor electrode
126 . . . COM electrode
128 . . . heater electrode
130 . . . gas detection element
137 . . . pump cell
145 . . . spacer
145c . . . gas detection chamber
150 . . . electromotive force cell
160 . . . heater element
182-184 . . . sensor connection terminal
185, 186 . . . heater connection terminal
193-195 . . . sensor lead wire
196, 197 . . . heater lead wire

DETAILED DESCRIPTION OF THE PREFERRED EMBODIMENTS

Next, an embodiment of the present invention will be described in greater detail with reference to the drawings. However, the present invention should not be construed as being limited thereto.

A. Schematic Configuration of Anomaly Diagnosing Apparatus:

FIG. 1 is a block diagram schematically showing the configuration of an anomaly diagnosing apparatus 10 for a gas sensor. As shown in FIG. 1, the anomaly diagnosing apparatus 10 of the present embodiment includes an anomaly diagnosing circuit 20, which has a CPU 21, RAM 22 and ROM 23; a heater control circuit 30 connected to the anomaly diagnosing circuit 20; and a display apparatus 40 connected to the anomaly diagnosing circuit 20. Three sensor lead wires 193, 194 and 195 extending from a gas sensor 100 are connected to the anomaly diagnosing circuit 20, and two heater lead wires 196 and 197 extending from the gas sensor 100 are connected to the heater control circuit 30.

A predetermined control program is stored in the ROM 23 of the anomaly diagnosing circuit 20. The CPU 21 loads this control program into the RAM 22 and executes it, to thereby realize anomaly diagnosing processing, described below. By executing the control program, the anomaly diagnosing circuit 20 functions as the measurement section and the diagnosing section of the present invention.

The display apparatus 40 displays the results of anomaly diagnosis performed for the gas sensor 100 by the anomaly diagnosing circuit 20. Any of various types of display apparatuses, such as a liquid crystal monitor, a CRT monitor, or a LED display, may be used as the display apparatus 40. In the case where the anomaly diagnosing apparatus 10 is mounted on a vehicle, a warning lamp on an instrument panel may be used as the display apparatus.

The heater control circuit 30 is a circuit for performing heating control (electricity supply control) for a heater element incorporated into the gas sensor 100. The heater control circuit 30 heats the heater element in accordance with an ON/OFF signal output from the anomaly diagnosing circuit 20. Notably, the heating control (electricity supply control) for the heater element is a known control (see, for example, U.S. Pat. No. 6,214,207, incorporated herein by reference) which is performed for activating a gas sensor element 120 formed of a solid electrolyte body described below. Therefore, the details of this control will not be described here.

Figure 2:
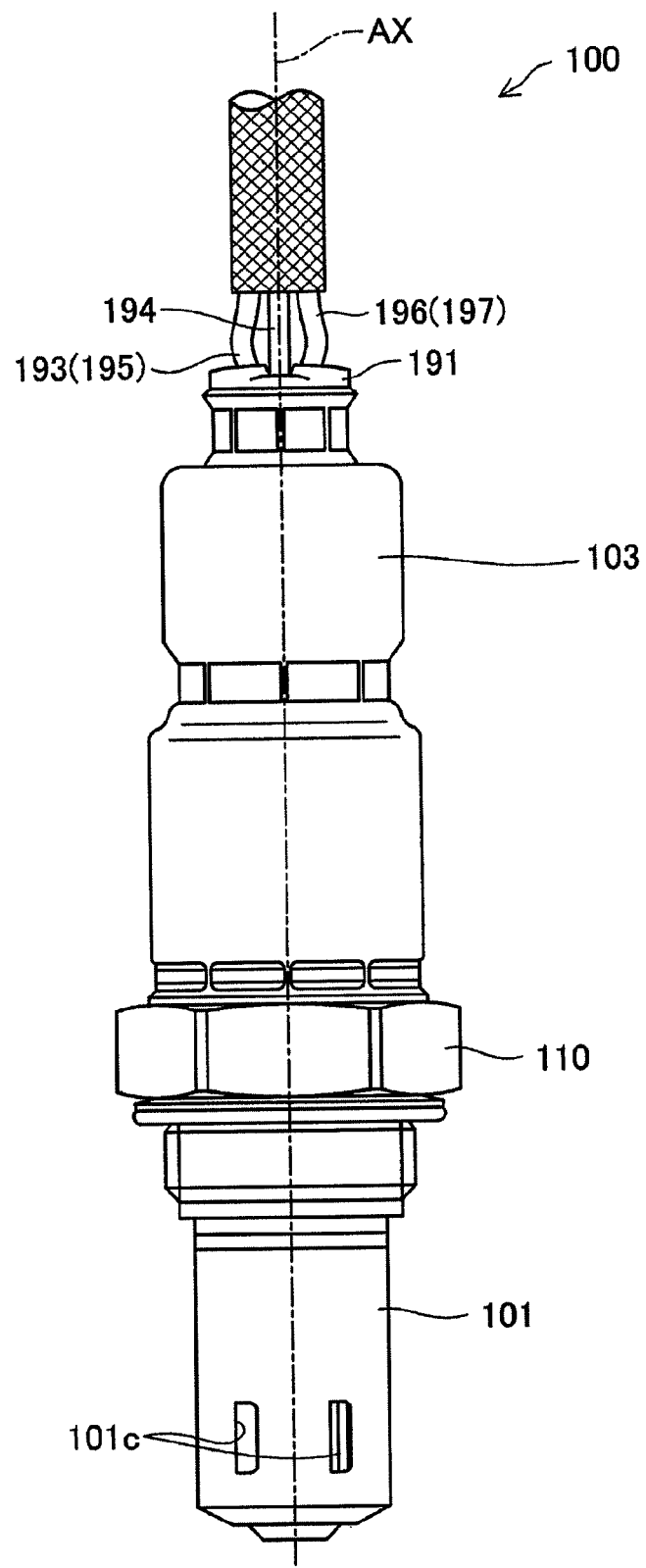
FIG. 2 is an external view of the gas sensor 100.
Figure 3:
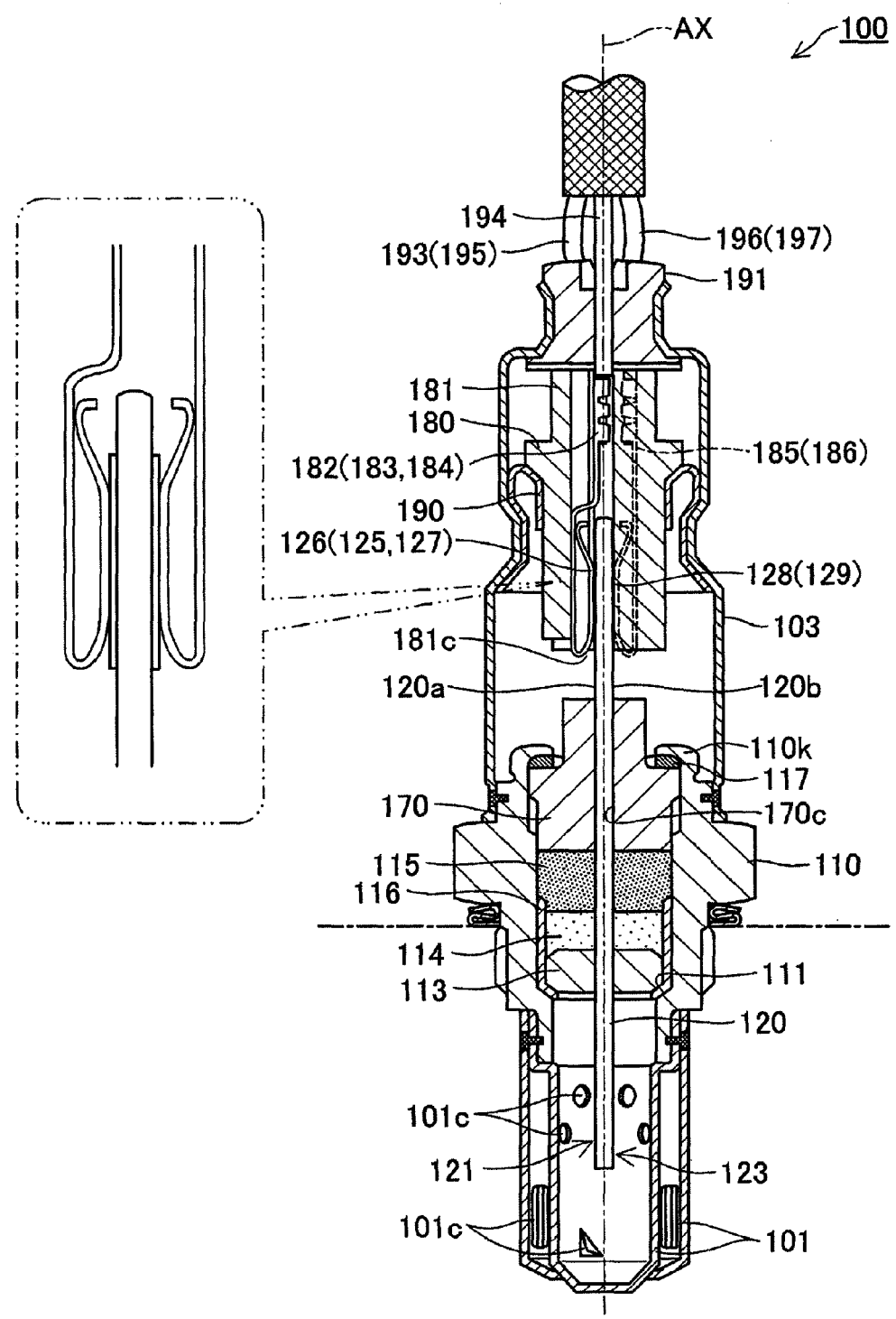
FIG. 3 is a sectional view of a gas sensor 100.

B. Structure of Gas Sensor:

FIG. 2 is an external view of the gas sensor 100, and FIG. 3 is a cross sectional view of the gas sensor 100. In FIGS. 2 and 3, the lower side corresponds to a tip end side along the direction of an axis AX, and the upper side corresponds to a base end side along the direction of the axis AX. This gas sensor 100 is configured as a full-range air-fuel ratio sensor which is attached to an exhaust pipe and which linearly detects the concentration of oxygen within exhaust gas so as to apply feedback-control to the air-fuel ratio of a gas mixture supplied to an internal combustion engine.

As shown in FIGS. 2 and 3, the gas sensor 100 includes a tubular metallic shell 110 extending along the direction of the axis AX; a plate-shaped gas sensor element 120 disposed within the metallic shell 110 and extending along the direction of the axis AX; a tubular ceramic sleeve 170 disposed within the metallic shell 110 and supporting the gas sensor element 120 inserted thereinto; and a connection body 180 attached to the base end side of the gas sensor element 120 and adapted to electrically connect the gas sensor element 120 with various lead wires.

As shown in FIG. 3, the gas sensor element 120 is disposed within the metallic shell 110 such that its tip end portion projects from the metallic shell 110 toward the tip end side, and its base end portion projects from the metallic shell 110 toward the base end side. A gas detection section 121 configured to detect the concentration of oxygen within exhaust gas and a heater section 123 configured to heat the gas detection section 121 are provided in the tip end portion of the gas sensor element 120. Three sensor electrodes (a Vs electrode 125, a COM electrode 126 and an Ip electrode 127 shown in FIG. 4), which are electrically connected to the gas detection section 121, are provided on a first plate face 120a of a base end portion of the gas sensor element 120; and two heater electrodes 128 and 129 (see FIG. 4), which are electrically connected to the heater section 123, are provided on a second plate face 120b of the base end portion of the gas sensor element 120. The specific structure of the gas sensor element 120 will be described below.

The metallic shell 110 assumes the form of a tube extending along the axial direction, and a step portion 111, which projects radially inward, is formed inside the metallic shell 110. Within the metallic shell 110, a tubular ceramic holder 113 formed of alumina, a first powder-charged layer 114 formed of talc powder, a second powder-charged layer 115 formed of talc powder, and the tubular ceramic sleeve 170 formed of alumina are disposed in this sequence from the tip end side toward the base end side. Further, a tubular metal cup 116, which is integrated with the gas sensor element 120 together with the ceramic holder 113 and the first powder-charged layer 114, is disposed within the metallic shell 110. Further, a crimp ring 117 is disposed between the ceramic sleeve 170 and the base end portion 110k of the metallic shell 110.

The ceramic holder 113 is disposed within the metal cup 116, and, on its tip end side, is engaged with the step portion 111 of the metallic shell 110 via the metal cup 116. The gas sensor element 120 penetrates the ceramic holder 113. Further, the entirety of the first powder-charged layer 114 and a portion of the second powder-charged layer 115 on the tip end side thereof are disposed within the metal cup 116. Notably, the second powder-charged layer 115 secures air-tightness between the metallic shell 110 and the gas sensor element 120.

The ceramic sleeve 170 assumes the form of a tube having a rectangular axial hole 170c which extends along the axis AX and forms a rectangular opening. The ceramic sleeve 170 supports the plate-shaped gas sensor element 120, which is inserted into the rectangular axial hole 170c. The ceramic sleeve 170 is fixed within the metallic shell 110 by means of bending the base end portion 110k of the metallic shell 110 radially inward, and crimping the base end portion 110k toward the base end surface of the ceramic sleeve 170 via the crimp ring 117.

A protector 101 assuming the foam of a double-walled tube having a closed bottom is fixed, through laser welding, to the tip end of the metallic shell 110 so as to cover the tip end portion of the gas sensor element 120 projecting from the metallic shell 110. The protector 101 has a plurality of introduction holes 101c formed at predetermined positions for introducing exhaust gas into the interior of the protector 101.

A tubular metal outer sleeve 103 is fixed, through laser welding, to the base end of the metallic shell 110. The connection body 180 is disposed inside the metal outer sleeve 103. This connection body 180 is composed of a separator 181 formed of ceramic, three sensor connection terminals 182, 183, 184 and two heater connection terminals 185, 186. The separator 181 accommodates the sensor connection terminals 182, 183, 184 and the heater connection terminals 185, 186 in an isolated condition such that the sensor connection terminals 182, 183, 184 and the heater connection terminals 185, 186 do not come into contact with one another.

The connection body 180 is attached to the base end of the gas sensor element 120 such that it is spaced from the above-mentioned ceramic sleeve 170. The base end portion of the gas sensor element 120, which projects from the base end of the ceramic sleeve 170, is inserted into an opening 181c of the separator 181. The sensor connection terminals 182, 183 and 184 elastically come into contact with the sensor electrodes 125, 126 and 127 of the gas sensor element 120, whereby the sensor connection terminals 182, 183 and 184 are electrically connected to the sensor electrodes 125, 126 and 127. Further, the heater connection terminals 185 and 186 elastically come into contact with the heater electrodes 128 and 129 of the gas sensor element 120, whereby the heater connection terminals 185 and 186 are electrically connected to the heater electrode 128 and 129. An enlarged view on the left side of FIG. 3 shows a state where these connection terminals are in contact with the electrodes provided on the gas sensor element 120, so as to facilitate understanding of the contact state.

An urging metal piece 190, which is disposed to surround the connection body 180 and assumes an approximately tubular shape, holds the connection body 180 within the metal outer sleeve 103 in a state in which the connection body 180 is urged toward a grommet 191, described below.

The grommet 191, which is formed of fluororubber and through which three sensor lead wires 193, 194 and 195 and two heater lead wires 196 and 197 are passed, is disposed inside a base end portion of the metal outer sleeve 103. Tip end portions of the sensor lead wires 193, 194 and 195 are inserted into the connection body 180 and fixed to the sensor connection terminals 182, 183 and 184 through crimping, whereby the sensor lead wires 193, 194 and 195 are electrically connected to the sensor connection terminals 182, 183 and 184. Further, tip end portions of the heater lead wires 196 and 197 are inserted into the connection body 180 and fixed to the heater connection terminals 185 and 186 through crimping, whereby the heater lead wires 196 and 197 are electrically connected to the heater connection terminals 185 and 186. The sensor lead wire 193 is connected to the Ip electrode 125 of the gas sensor element 120 via the sensor connection terminal 182, and the sensor lead wire 194 is connected to the COM electrode 126 of the gas sensor element 120 via the sensor connection terminal 183. Further, the sensor lead wire 195 is connected to the Vs electrode 127 of the gas sensor element 120 via the sensor connection terminal 184.

Figure 4:
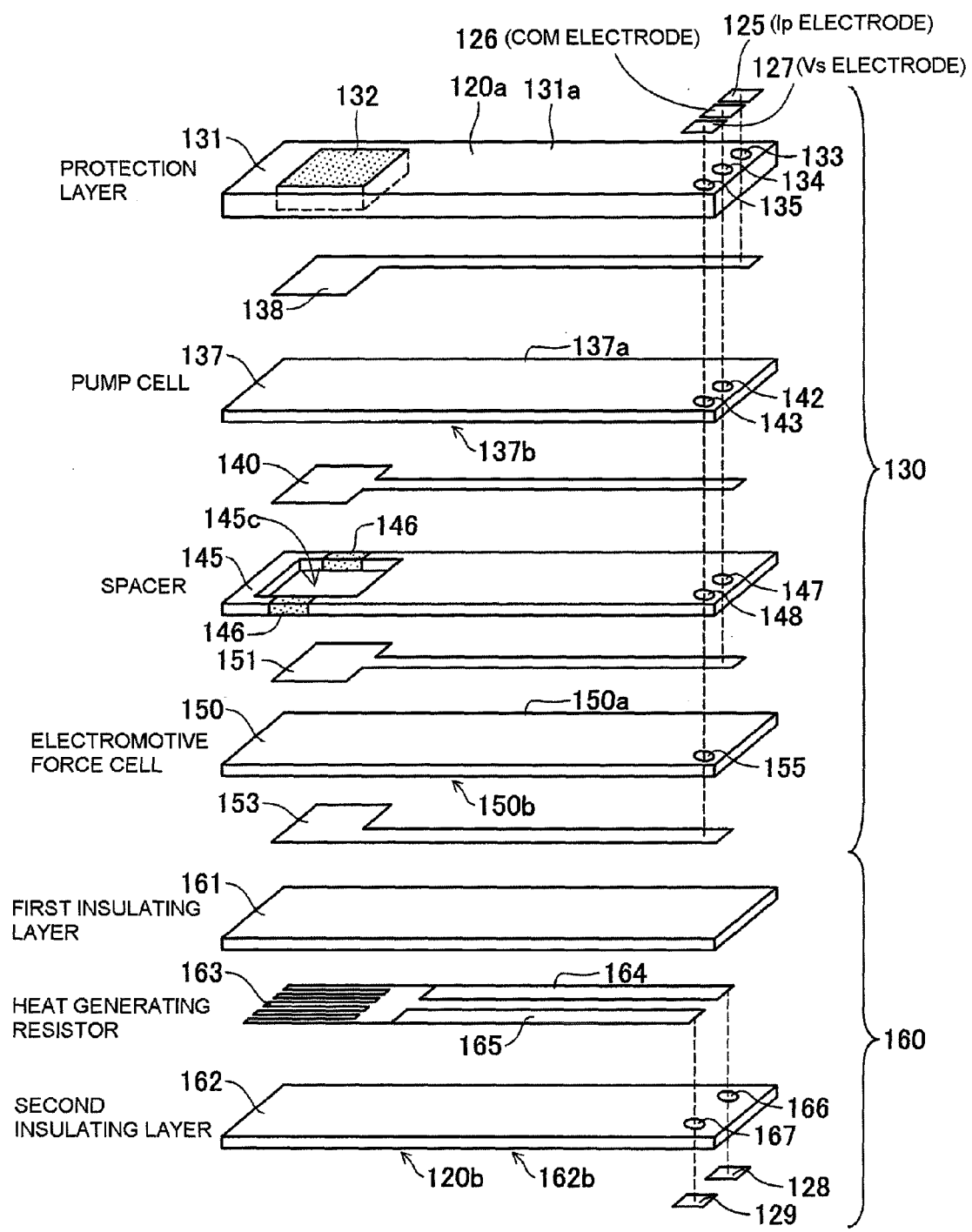
FIG. 4 is an exploded perspective view of a gas sensor element 120.

C. Structure of Gas Sensor Element:

FIG. 4 is an exploded perspective view of the gas sensor element 120. The gas sensor element 120 includes a plate-shaped detection element 130 extending along the axial direction (left-right direction in FIG. 4), and a plate-shaped heater element 160 extending along the axial direction, which are stacked and unified through firing. Notably, in FIG. 4, the left-hand side corresponds to the tip end side in FIGS. 2 and 3, and the right-hand side corresponds to the base end side in FIGS. 2 and 3.

The detection element 130 is composed of a protection layer 131, a pump cell 137, a spacer 145 and an electromotive force cell 150, each of which assumes a plate-like shape and which are stacked in this sequence from the first plate face 120a side toward the second plate face 120b side.

The protection layer 131 is mainly formed of alumina. A porous body 132 is formed in a tip end portion of the protection layer 131. The above-described three sensor electrodes; i.e., the Ip electrode 125, the COM electrode 126 and the Vs electrode 127, are formed on a first face 131a of the protection layer 131, which constitutes the first plate face 120a of the gas sensor element 120, in the vicinity of the base end thereof. In this manner, the three sensor electrodes are arranged at predetermined intervals along a direction perpendicular to the axial direction. As indicated by broken lines in FIG. 4, the Ip electrode 125, the COM electrode 126, and the Vs electrode 127 are electrically connected to three via conductors 133, 134, and 135, respectively, which are formed in the protection layer 131 in the vicinity of the base end thereof such that the via conductors penetrate the protection layer 131.

The pump cell 137 includes a solid electrolyte body mainly formed of zirconia. Two via conductors 142 and 143 are formed in the pump cell in the vicinity of the base end thereof such that the via conductors penetrate the pump cell. These via conductors 142 and 143 are electrically connected to the via conductors 134 and 135 formed in the protection layer 131 to pass therethrough.

A first electrode portion 138, which is mainly formed of Pt, is porous, and has a rectangular shape, is formed on a first face 137a (on the upper side in FIG. 4) of the pump cell 137. This first electrode portion 138 is electrically connected to the via conductor 133 formed in the protection layer 131 to pass therethrough. Therefore, the first electrode portion 138 is electrically connected to the Ip electrode 125 via the via conductor 133. The first electrode portion 138 is exposed to exhaust gas via the porous body 132 provided in the protection layer 131.

A second electrode portion 140, which is mainly formed of Pt, is porous, and has a rectangular shape, is formed on a second face 137b (on the lower side in FIG. 4) of the pump cell 137. This second electrode portion 140 is electrically connected to the via conductor 142 formed in the pump cell 137 to pass therethrough. Therefore, the second electrode portion 140 is electrically connected to the COM electrode 126 via the via conductors 142 and 134.

The spacer 145 is mainly formed of alumina, and has a rectangular opening in a tip end portion thereof. The opening forms a gas detection chamber 145c when the spacer 145 is stacked together with the pump cell 137 and the electromotive force cell 150 such that the spacer 145 is sandwiched between the pump cell 137 and the electromotive force cell 150. Portions of opposite side walls of the gas detection chamber 145c are formed of porous bodies 146 which secure passage of air between the interior and exterior of the gas detection chamber 145c. The porous bodies 146 are formed of porous alumina. Two via conductors 147 and 148 are formed in the spacer 145 in the vicinity of the base end thereof such that the via conductors penetrate the spacer 145. The via conductor 147 is electrically connected to the second electrode portion 140. Further, the via conductor 148 is electrically connected to the via conductor 143 formed to pass through the above-described pump cell 137.

The electromotive force cell 150 is a solid electrolyte body mainly formed of zirconia. A via conductor 155 is formed in the electromotive force cell 150 in the vicinity of the base end thereof such that the via conductor penetrates the electromotive force cell 150. The via conductor 155 is electrically connected to the via conductor 148 formed to pass through the spacer 145.

A third electrode portion 151, which is mainly formed of Pt, is porous, and has a rectangular shape, is formed on a first face 150a (on the upper side in FIG. 4) of the electromotive force cell 150. This third electrode portion 151 is electrically connected to the via conductor 147 formed to pass through the spacer 145. Therefore, the third electrode portion 151 is electrically connected to the COM electrode 126 via the via conductor 147, the second electrode portion 140, the via conductor 142, and the via conductor 134. That is, the third electrode portion 151 and the second electrode portion 140, which are commonly connected to the COM electrode 126, assume the same electrical potential.

A fourth electrode portion 153, which is mainly formed of Pt, is porous, and has a rectangular shape, is formed on a second face 150b (on the lower side in FIG. 4) of the electromotive force cell 150. This fourth electrode portion 153 is electrically connected to the via conductor 155 formed to pass through the electromotive force cell 150. Therefore, the fourth electrode portion 153 is electrically connected to the Vs electrode 127 via the via conductor 155, the via conductor 148, the via conductor 143 and the via conductor 135.

The heater element 160 includes a first insulating layer 161 and a second insulating layer 162 which are formed of alumina, assume a plate-like shape, and are stacked in this sequence from the first plate face 120a side toward the second plate face 120b side. A heat generating resistor 163 and heater lead portions 164 are formed between the first insulating layer 161 and the second insulating layer 162. The heat generating resistor 163 is mainly formed of Pt, assumes a zigzag shape, and is located on the tip end side. The heater lead portions 164 and 165 are connected to opposite ends of the heat generating resistor 163, and extend to the base end side.

Two via conductors 166 and 167 are formed in the second insulating layer 162 in the vicinity of the base end thereof such that the conductors 166 and 167 penetrate the second insulating layer 162. Further, the above-described two heater electrodes 128 and 129 are formed on a second face 162b, which constitutes the second plate face 120b of the gas sensor element 120, in the vicinity of the base end thereof such that the two heater electrodes are arranged along a direction perpendicular to the axial direction. Of these heater electrodes, the heater electrode 128 is electrically connected to the heater lead portion 164 by means of the via conductor 166. Further, the heater electrode 129 is electrically connected to the heater lead portion 165 by means of the via conductor 167.

Operation of the gas sensor 100 having the above-described structure in ordinary use will be described for reference. At the time of ordinary use of the gas sensor 100, the heater control circuit 30 is caused to heat the heater element 160 to several hundred degrees (e.g., 700 to 800° C.) so as to activate the pump cell 137 and the electromotive force cell 150, and a minute current Icp (about 15 µA) is supplied to the electromotive force cell 150 via the Vs electrode 127 so that the fourth electrode portion 153 functions as an oxygen reference chamber. In this state, when the air-fuel ratio of the atmosphere within the gas detection chamber 145c is maintained at the stoichiometric ratio, a voltage of 450 mV is generated between the electromotive force cell 150 and the oxygen reference chamber in which the concentration of oxygen is maintained substantially constant. By use of a predetermined electric circuit having a well-known configuration, the current Ip supplied to the pump cell 137 is adjusted such that the voltage Vs of the electromotive force cell 150 becomes 450 mV, whereby the air-fuel ratio of the atmosphere within the gas detection chamber 145c is maintained at the stoichiometric ratio. When the gas sensor 100 is operated in this manner, the concentration of oxygen within the exhaust gas can be measured on the basis of the value of the current Ip required to maintain the air-fuel ratio of the atmosphere within the gas detection chamber 145c at the stoichiometric ratio. Notably, in the anomaly diagnosing processing described below, such control for detection of oxygen concentration is not carried out.

D. Anomaly Diagnosing Processing:

Next, anomaly diagnosing processing will be described for diagnosing the gas sensor 100 having the above-described structure so as to determine whether or not the gas sensor 100 is anomalous. In the present embodiment, the anomaly diagnosing processing determines whether or not a Vs line connected to the electromotive force cell 150 is anomalous. The Vs line refers to an electric path which extends from the anomaly diagnosing apparatus 10; reaches the electromotive force cell 150 via the sensor lead wire 195, the sensor connection terminal 184, the Vs electrode 127, and the fourth electrode portion 153; and returns therefrom to the anomaly diagnosing apparatus 10 via the third electrode portion 151, the COM electrode 126, the sensor connection terminal 183, and the sensor lead wire 194.

Figure 5:
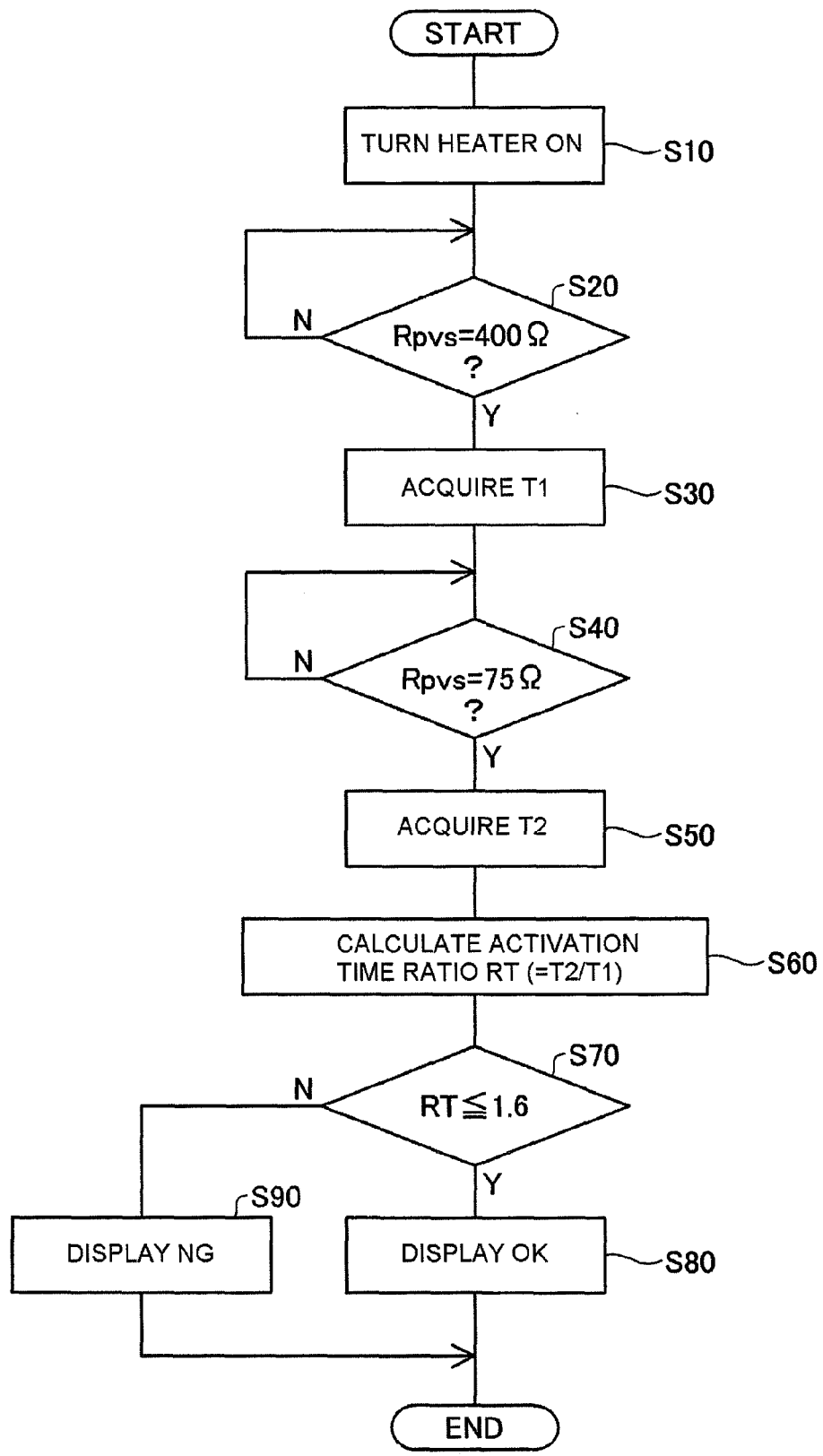
FIG. 5 is a flowchart of an anomaly diagnosing processing.

FIG. 5 is a flowchart of the anomaly diagnosing processing executed by the CPU 21 of the anomaly diagnosing circuit 20. The anomaly diagnosing processing shown in FIG. 5 is executed in an inspection stage of a production line for the gas sensor 100, and in a state where the gas sensor 100 is placed in the atmosphere at a room temperature and is connected to the anomaly diagnosing apparatus 10.

When execution of this anomaly diagnosing processing is started, the CPU 21 first controls the heater control circuit 30 so as to start heating of the gas sensor element 120 (heating control) (step S10). Simultaneously with the start of the heating of the gas sensor element 120, the CPU 21 starts the counting of a timer. When the gas sensor element 120 is heated, the flowability of oxygen ions within the electromotive force cell 150 increases gradually, and the impedance (internal resistance) of the electromotive force cell 150 decreases.

Figure 6:
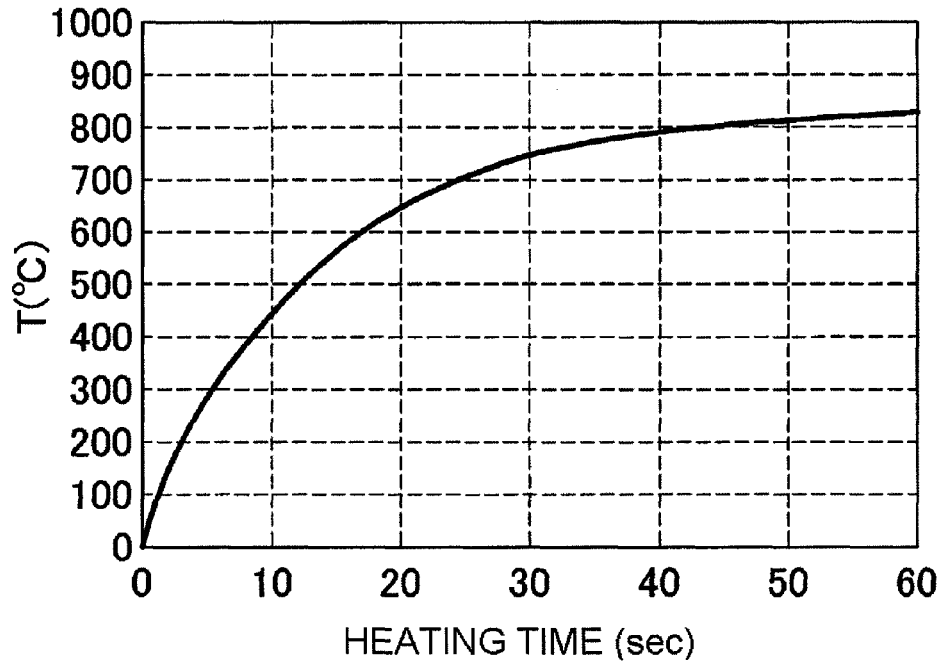
FIG. 6 is a graph showing an example change in the temperature of the gas sensor element 120.
Figure 7:
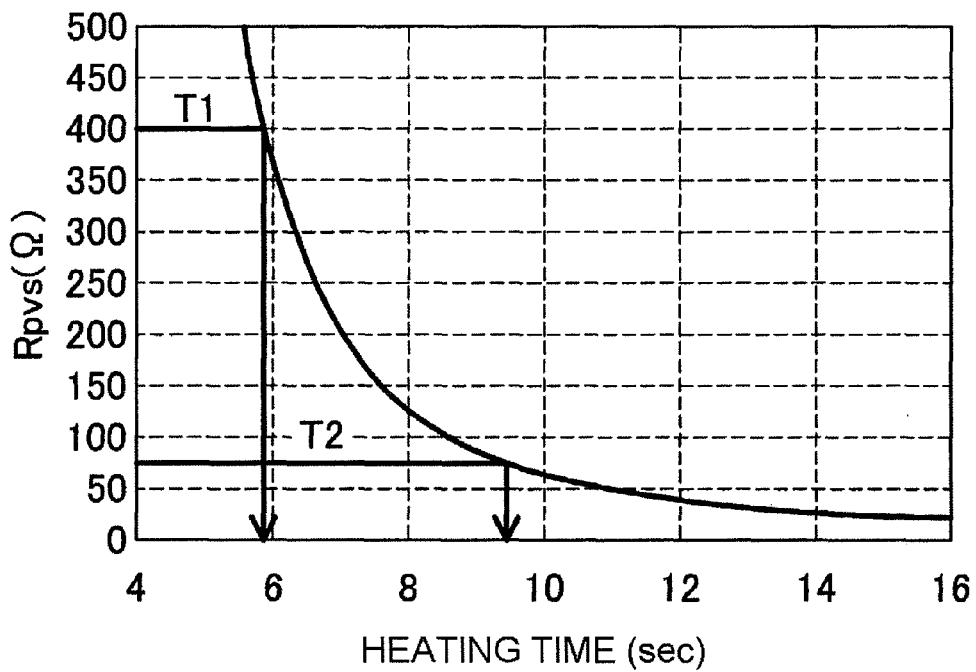
FIG. 7 is a graph showing an example change in the internal resistance Rpvs of a Vs line.

FIG. 6 is a graph showing an example change in the temperature of the gas sensor element 120. FIG. 7 is a graph showing an example change in the internal resistance Rpvs of the Vs line with heating time. As shown in these drawings, the higher the temperature of the gas sensor element 120; i.e., the lower the resistance of the electromotive force cell 150, the smaller the increase in the temperature of the gas sensor element 120 per unit time. Notably, at the time of start of the anomaly diagnosing processing, since the electromotive force cell 150 is at room temperature, the electromotive force cell 150 functions as an insulator. Therefore, as shown in FIG. 7, the internal resistance Rpvs of the Vs line at the time of start of the anomaly diagnosing processing is infinite.

Subsequently, the CPU 21 supplies a current pulse (or voltage pulse) having a period of 60 μs to the Vs line as a predetermined detection signal, to thereby measure the internal resistance Rpvs, which is an electrical characteristic of the Vs line. Specifically, the CPU 21 supplies a transient current pulse (or voltage pulse) to the Vs line, detects the change in voltage (or current) output via the Vs line as a response signal, and measures the internal resistance Rpvs of the electromotive force cell 150 from the detected change in voltage (current) and the magnitude of the current pulse (or voltage pulse). Notably, the measurement of the internal resistance Rpvs is performed using an unillustrated, well-known internal resistance detection circuit (see, for example, U.S. Pat. No. 6,120,677, incorporated herein by reference) separately provided in the anomaly diagnosing apparatus 10. This measurement is executed at predetermined intervals (e.g., at intervals of 10 ms).

Subsequently, the CPU 21 determines whether or not the measured internal resistance Rpvs has decreased to 400Ω (step S20). When the CPU 21 determines that the internal resistance Rpvs has decreased to 400Ω, the CPU 21 acquires the value of the timer at that instant as a first activation time T1 (see FIG. 7) (step S30). Meanwhile, when the internal resistance Rpvs has not yet reached 400Ω, the CPU 21 repeats the processing of step S20 until the internal resistance Rpvs reaches 400Ω. When the gas sensor 100 is normal, the first activation time T1 falls within a range of about 3 seconds to about 8 seconds, but varies due to individual differences among sensors.

After having acquired the first activation time T1, subsequently, the CPU 21 determines whether or not the internal resistance Rpvs has decreased to 75Ω (step S40). The reason why 75Ω is used as a determination criterion is that, at the time of ordinary use of the gas sensor 100, the electric supply control to the heater is performed such that the internal resistance Rpvs of the Vs line (electromotive force cell 150) becomes about 75Ω.

When the internal resistance Rpvs is determined to have decreased to 75Ω, the CPU 21 acquires the value of the timer at that instant as a second activation time T2 (see FIG. 7) (step S50). Meanwhile, when the internal resistance Rpvs has not yet reached 75Ω, the CPU 21 repeatedly performs the processing of step S40 until the internal resistance Rpvs reaches 75Ω. When the gas sensor 100 is normal, the second activation time T2 falls within a range of about 4 seconds to about 12 seconds, but may vary due to individual differences among sensors. Notably, the anomaly diagnosing processing may be modified as follows. When a time in excess of the upper limit of the variation range of the first activation time T1 or the second activation time T2 elapses in step S20 or step S40, the CPU 21 determines at that point in time that the gas sensor 100 is anomalous. Specifically, the anomaly diagnosing processing may be modified such that, when 15 seconds elapses in step S20 or 20 seconds elapses in step S40, the processing skips to step S90 so as to display on the display apparatus 40 a message indicating that the gas sensor 100 is anomalous.

After having acquired the second activation time T2, the CPU 21 obtains an activation time ratio RT (=T2/T1), which is the ratio of the second activation time T2 to the first activation time T1 (step S60), and determines whether or not the activation time ratio RT is equal to or less than 1.6, which is a predetermined threshold value (step S70). When the activation time ratio RT is equal to or less than 1.6, the CPU 21 determines that the internal resistance Rpvs of the Vs line is normal, and displays on the display apparatus 40 a message indicating that the gas sensor 100 is normal (OK), as a result of diagnosis (step S80). Meanwhile, when the activation time ratio RT is greater than 1.6, the CPU 21 determines that the internal resistance Rpvs of the Vs line is anomalous, and displays on the display apparatus 40 a message indicating that the gas sensor 100 is anomalous (NG), as a result of diagnosis (step S90). By means of the above-described series of processes, the anomaly diagnosing apparatus 10 can determine whether or not the Vs line of the gas sensor 100 is anomalous.

Figure 8:
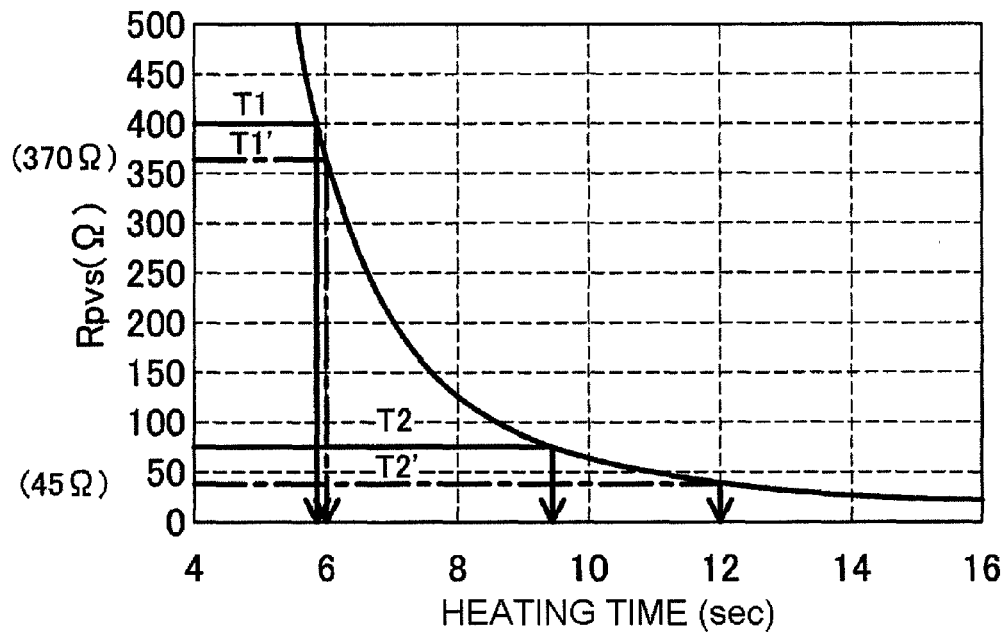
FIG. 8 is a graph showing examples of a first activation time T1 and a second activation time T2 for the case where a contact resistance is present in the Vs line.

Here, the reason why the Vs line can be determined to be anomalous or normal on the basis of the ratio of the second activation time T2 to the first activation time T1 (the activation time ratio RT) will be described with reference to FIGS. 8 to 10. FIG. 8 shows examples of the first activation time T1 and the second activation time T2 for the case where a contact resistance of 30Ω is present between the sensor connection terminal 184 and the Vs electrode 127.

In the case where a contact resistance of 30Ω is present in series with the sensor connection terminal 184 and the Vs electrode 127, the measured resistance does not reach a value of as low as 400Ω, which is the determination criterion for acquiring the first activation time T1, until the internal resistance Rpvs decreases to 370Ω. Therefore, as shown in FIG. 8, in the case where the Vs line includes the series contact resistance, the first activation time T1 becomes longer by a time less than about one second, as compared with the case where the Vs line is normal (negligible contact resistance). Further, in the case where a contact resistance of 30Ω is present between the sensor connection terminal 184 and the Vs electrode 127, the measured resistance does not reach 75Ω, which is the determination criterion for acquiring the second activation time T2, until the internal resistance Rpvs decreases to 45Ω. Therefore, as shown in FIG. 8, in the case where the Vs line includes the series contact resistance, the second activation time T2 becomes longer by about several seconds, as compared with the case where the Vs line is normal.

An experiment was performed in which a pseudo contact resistance was introduced by means of intentionally inserting a variable series resistor into the Vs line of one gas sensor 100, and the first activation time T1 and the second activation time T2 were measured while the contact resistance was varied (by means of the variable resistor). FIG. 9 shows the results of the experiment. In FIG. 9, the horizontal axis represents the contact resistance which was intentionally varied, and the vertical axis represents the first activation time T1 and the second activation time T2. As shown in FIG. 9, even when the contact resistance is changed, the first activation time T1 does not change very much; however, the second activation time T2 becomes noticeably longer with increasing contact resistance.

However, as described above, even among normal gas sensors 100, the first activation time T1 varies within the range of 3 seconds to 8 seconds, and the second activation time T2 varies within the range of 4 seconds to 12 seconds due to individual differences therebetween. That is, the increases in the first activation time T1 and the second activation time T2 shown in FIG. 9 fall within the ranges of variation of activation times among the gas sensors.

Figure 9:
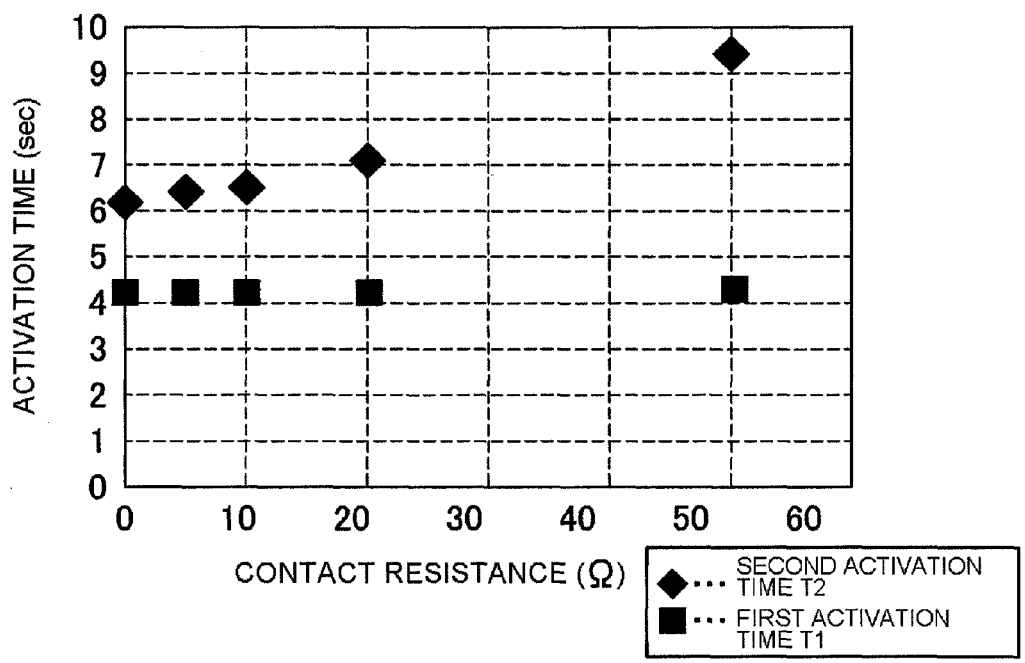
FIG. 9 is a graph showing the results of an experiment in which a variable series resistance was intentionally introduced into the Vs line (so as to vary the effective contact resistance), and the first activation time T1 and the second activation time T2 were measured as a function of contact resistance.

In view of the above, on the basis of the results of the experiment shown in FIG. 9, the ratio of the second activation time T2 to the first activation time T1 was obtained as an activation time ratio RT. FIG. 10 shows the results. Specifically, a plurality of sample gas sensors 100 were prepared; and an experiment similar to the experiment whose results are shown in FIG. 9 was performed so as to obtain the activation time ratios RT of the sample gas sensors 100. FIG. 10 shows the activation time ratios RT of the sample gas sensors 100. FIG. 10 shows, for each sample, an approximation line which connects activation time ratios RT corresponding to values of the contact resistance within the range of 0Ω to 50Ω. As shown in FIG. 10, the variation of the activation time ratios RT obtained for the plurality of samples falls within a relatively narrow range.

Figure 10:
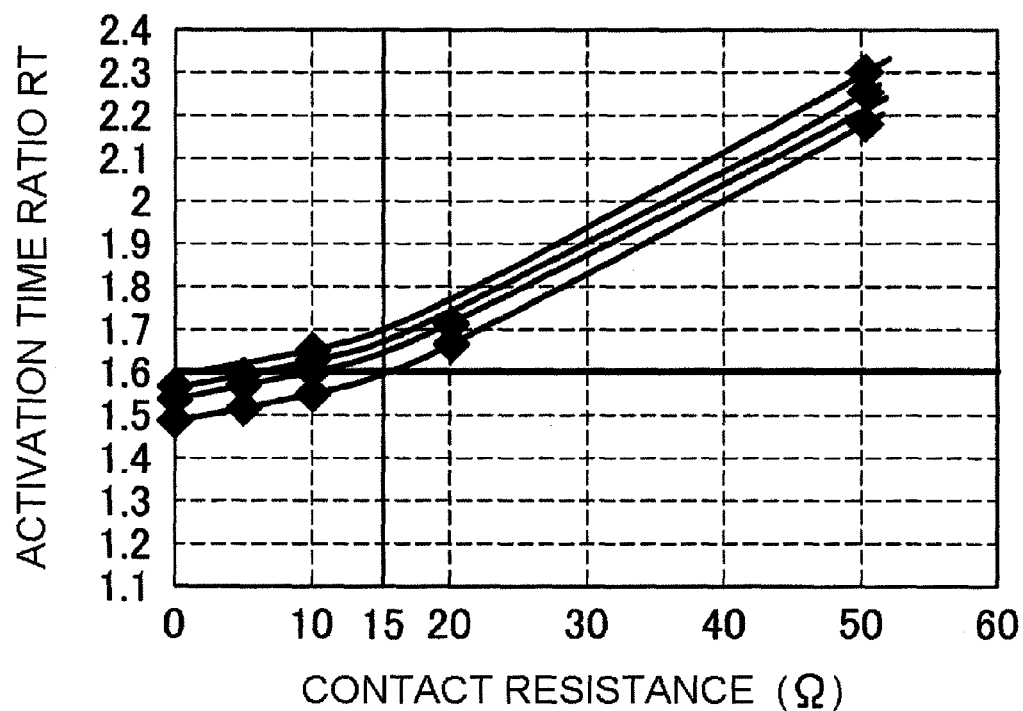
FIG. 10 is a graph showing the results of an experiment similar to the experiment whose results are shown in FIG. 9 and which was performed for a plurality of gas sensors 100.

As shown in FIG. 10, in the experiment in the present embodiment, when the contact resistance was 0Ω, the maximum value of the activation time ratio RT was 1.6. A contact resistance at which the minimum value of the activation time ratio RT becomes 1.6 was obtained on the basis of the graph shown in FIG. 10. The contact resistance thus obtained was about 15Ω. That is, in consideration of variation of the activation time ratio RT among the samples, when the contact resistance is 15Ω or greater, the contact resistance can be determined not to be 0Ω. Accordingly, a gas sensor 100 whose activation time ratio is 1.6 or higher can be determined to have a contact resistance of 15Ω or greater in the Vs line. In such a case, the above-described anomaly diagnosing processing determines that the gas sensor 100 is anomalous.

Incidentally, when the internal resistance Rpvs of the Vs line is measured after the electromotive force cell 150 enters a stable activated state as a result of heating the gas sensor element 120 for a sufficiently long time, the presence of a contact resistance is easily detected by comparing the measured internal resistance to a predetermine threshold value. As shown in FIG. 6, the electromotive force cell 150 requires a time of about 30 seconds to 60 seconds after the start of heating so as to enter a stable activated state. However, as shown in FIGS. 8 to 10, the anomaly diagnosing processing of the present embodiment can end anomaly diagnosis within about 7 to 8 seconds (or within ten and some seconds in the longest case) after the start of heating, even when the activation times vary in accordance with the individual difference of the gas sensors 100. As a result, according to the present embodiment, diagnosis for determining whether or not the Vs line is anomalous can be performed at a practical speed, for example, in an inspection stage of a production line for the gas sensor 100 or at the time of startup of a vehicle.

Notably, in the present embodiment, diagnosis is performed so as to determine whether or not the Vs line of the gas sensor 100 is anomalous. However, in the same manner, diagnosis may be performed so as to determine whether or not the Ip line of the gas sensor 100 is anomalous. The Ip line is an electrical path which extends from the anomaly diagnosing apparatus 10, reaches the pump cell 137 via the sensor lead wire 193, the sensor connection terminal 182, the Ip electrode 127, and the first electrode portion 138, and returns therefrom to the anomaly diagnosing apparatus 10 via the second electrode portion 140, the COM electrode 126, the sensor connection terminal 183 and the sensor lead wire 194.

Figure 11:
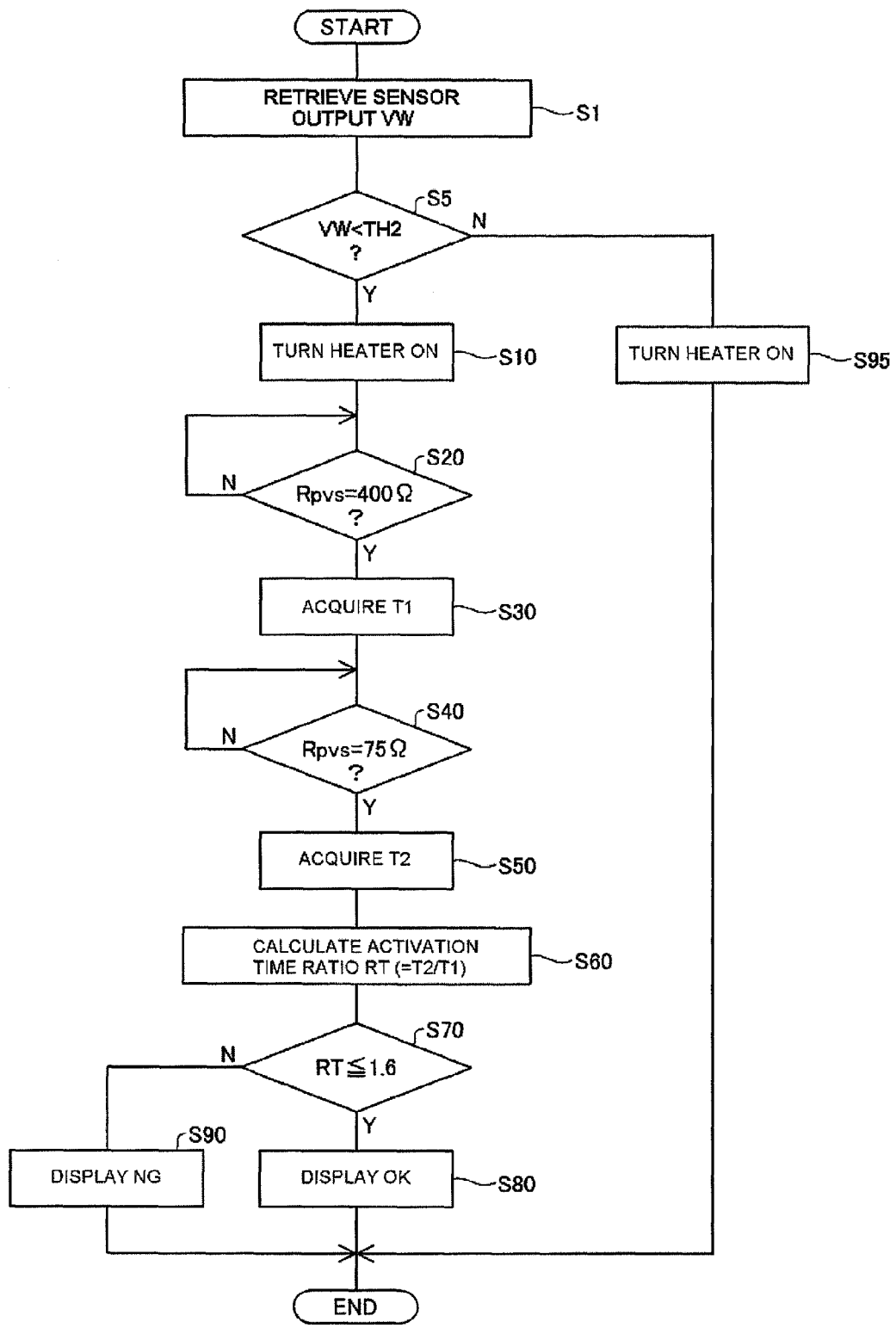
FIG. 11 is a flowchart showing an anomaly diagnosing processing when the gas sensor 100 is installed in the exhaust pipe of an internal combustion engine.

FIG. 5 is a flowchart which shows the anomaly diagnosing processing executed at an inspection stage of a production line for the gas sensor 100, and FIG. 11 is a flowchart which shows the anomaly diagnosing processing when the gas sensor 100 and the anomaly diagnosing apparatus 10 are installed in an exhaust pipe of vehicle (an internal combustion engine). When the anomaly diagnosing processing shown in FIG. 11 begins execution, CPU 21 reads a sensor output VW from a coolant temperature sensor not shown in FIG. 1 (Step S1). Generally, since the temperature of chilled water for an internal combustion engine correlates to the temperature of the gas sensor 100 (gas sensor element 120), the sensor output VW relating to the temperature of the chilled water is used as the sensor temperature parameter of the gas sensor 100 (gas sensor element 120) in the anomaly diagnosing processing shown in FIG. 11. The sensor temperature estimation section of the present invention corresponds to the combination of this step S1 and step S5 described below.

Next, CPU 21 determines whether the sensor output VW is lower than a predetermined threshold temperature level TH2 (step S5). The threshold temperature level TH2 is set to a temperature (e.g., 30° C.) equivalent to a cold sate of the internal combustion engine. This is because if the water temperature is 30° C. or lower, the temperature of the gas sensor 100 (gas sensor element 120) is also known to have decreased to 50° C. or lower since the last operation. Therefore, the internal resistance of the gas sensor should also be sufficiently high so as to allow for accurate anomaly diagnosis. When the sensor output VW is determined to be lower than the predetermined threshold temperature level TH2 in step S5, the sensor temperature estimation section estimates that the temperature of the gas sensor element 120 has been cooled to the predetermined temperature or lower (50° C. or lower). The anomaly diagnosing processing then proceeds to step S10. In step S10, the diagnosing section controls the heater controlling circuit 30 to begin heating of the gas sensor element 120.

After step S10, steps S20 to S90 are executed in the same way as in the flowchart shown in FIG. 5. Because process steps S20 to S90 have already been described, their description is not repeated.

On the other hand, when the sensor output VW is determined to be equal to or higher than a predetermined threshold temperature level TH2 in step S5, the temperature of the gas sensor element 120 is estimated to be higher than the predetermined temperature. The processing then goes to step S95. In step S95, the diagnosing section controls the heater controlling circuit 30 to begin heating the gas sensor element 120, and then the anomaly diagnosing processing is completed. Therefore, when the sensor output VW is determined to be equal to or higher than the predetermined threshold temperature level TH2 and the temperature of the gas sensor element 120 is estimated to be higher than the predetermined temperature, accuracy of the anomaly diagnosis for the gas sensor 100 by use of the activation time ratio RT may be compromised and is discontinued.

An embodiment of the present invention has been described above; however, the present invention is not limited thereto, and various configurations may be employed without departing from the spirit and scope of the invention.

For example, in the above-described embodiment, diagnosis is performed so as to determine whether or not the full-range air-fuel ratio sensor is anomalous. However, the present invention can be applied to other types of gas sensors such as a zirconia-type oxygen sensor and an $NO_X$ sensor, so long as the gas sensor employs a solid electrolyte as a sensor element.

Further, in the above-described embodiment, the internal resistance which serves as the determination criterion for acquiring the first activation time T1 is set to 400Ω, and the internal resistance which serves as the determination criterion for acquiring the second activation time T2 is set to 75Ω. However, the determination criteria are not limited to these resistances, and may be two other different resistances. In order to accurately and quickly perform diagnosis for determining the presence/absence of an anomaly on the basis of the activation time ratio RT, preferably, the internal resistance which serves as the determination criterion for acquiring the second activation time T2 is set to 100Ω or less (preferably, a value within a range of 50Ω to 100Ω inclusive), and the internal resistance which serves as the determination criterion for acquiring the first activation time T1 is set to a value greater than the first-mentioned internal resistance by 250Ω or more, in consideration of the declining rate of the internal resistance Rpvs shown in FIGS. 7 and 8.

This application is based on Japanese Patent Application No. 2008-257446 filed Oct. 2, 2008, incorporated herein by reference in its entirety.

What is claimed is:

1. An anomaly diagnosing method for a gas sensor which diagnoses an anomaly thereof, the gas sensor comprising a gas sensor element which includes a solid electrolyte and electrodes for outputting a signal representing an electrical characteristic of the solid electrolyte; connection terminals which contact the electrodes so as to lead the signal outside the gas sensor; and a heater which heats the solid electrolyte, the method comprising:
    heating the solid electrolyte by use of the heater;
    outputting a detection signal for detecting an internal resistance of the gas sensor through the solid electrolyte and via the connection terminals and the electrodes, and measuring the internal resistance of the gas sensor on the basis of a response signal which is input via the connection terminals in response to the output of the detection signal; and
    obtaining, after the start of heating of the solid electrolyte by use of the heater, a first time required for the measured internal resistance to reach a first resistance and a second time required for the measured internal resistance to reach a second resistance different from the first resistance, and determining whether or not the gas sensor is anomalous by comparing a predetermined threshold value with a ratio of the first to second times.

2. The anomaly diagnosing method for a gas sensor according to claim 1, wherein the second resistance is 100Ω or less, and the first resistance is greater than the second resistance by 250Ω or more.

3. The anomaly diagnosing method for a gas sensor according to claim 1, which further comprises estimating, before the heater control section begins control of the heater, whether the gas sensor is at a predetermined temperature or lower with reference to a sensor temperature parameter, and determining whether or not the gas sensor is anomalous only when the gas sensor is determined to be at the predetermined temperature or lower.

4. An anomaly diagnosing apparatus for a gas sensor which diagnoses an anomaly thereof, the gas sensor comprising a gas sensor element which includes a solid electrolyte and electrodes for outputting a signal representing an electrical characteristic of the solid electrolyte; connection terminals which contact the electrodes so as to lead the signal outside the gas sensor; and a heater which heats the solid electrolyte, the anomaly diagnosing apparatus comprising:
    a heater control section which controls the heater;
    a measurement section which outputs a detection signal for detecting an internal resistance of the gas sensor through the solid electrolyte and via the connection terminals and the electrodes and which measures the internal resistance of the gas sensor on the basis of a response signal which is input via the connection terminals in response to the output of the detection signal; and
    a diagnosing section programmed to heat the solid electrolyte by use of the heater control section, and programmed to obtain, after the start of heating, a first time required for the internal resistance, as measured by the measurement section, to reach a first resistance and a second time required for the internal resistance to reach a second resistance different from the first resistance, and programmed to determine whether or not the gas sensor is anomalous by comparing a predetermined threshold value with a ratio of the first to second times.

5. The anomaly diagnosing apparatus for a gas sensor according to claim 4, wherein the second resistance is 100Ω or less, and the first resistance is greater than the second resistance by 250Ω or more.

6. The anomaly diagnosing apparatus for a gas sensor according to claim 4, wherein the anomaly diagnosing apparatus further comprises a sensor temperature estimation section programmed to estimate, before the heater control section begins control of the heater, whether the gas sensor is at a predetermined temperature or lower with reference to a sensor temperature parameter, and is programmed to allow the diagnosing section to execute the gas sensor diagnosis only when the sensor temperature estimation section determines that the gas sensor is at the predetermined temperature or lower.

* * * * *